United States Patent [19]

Bollé

[11] Patent Number: 5,410,763
[45] Date of Patent: May 2, 1995

[54] EYESHIELD WITH DETACHABLE COMPONENTS

[75] Inventor: Maurice Bollé, Oyonnax, France

[73] Assignee: Etablissments Bolle, Oyonnax, France

[21] Appl. No.: 16,742

[22] Filed: Feb. 11, 1993

[51] Int. Cl.⁶ .............................................. A61F 9/02
[52] U.S. Cl. .......................................... 2/436; 2/439; 2/443; 2/444; 2/452
[58] Field of Search .................... 2/439, 426, 431, 432, 2/435, 436, 437, 442, 443, 444, 445, 446, 447, 452, 427, 228, 429, 430; 128/201.12; 351/47, 158, 123, 119, 120

[56] References Cited

U.S. PATENT DOCUMENTS

| | | |
|---|---|---|
| D. 310,839 | 9/1990 | Bollé . |
| D. 322,082 | 12/1991 | Bollé . |
| 805,401 | 11/1905 | Zarbaugh . |
| 2,126,739 | 8/1938 | Fischer . |
| 2,179,286 | 11/1939 | English . |
| 2,406,608 | 8/1946 | Joyce . |
| 2,406,998 | 9/1946 | DuBois . |
| 2,617,100 | 11/1952 | Moeller . |
| 2,648,843 | 8/1953 | Hirschmann . |
| 2,774,279 | 12/1956 | Olson et al. . |
| 2,905,172 | 9/1959 | Rodenhouse ................ 128/201.12 |
| 2,936,450 | 5/1960 | Luisada . |
| 3,004,535 | 10/1961 | Nielson ........................ 128/201.12 |
| 3,051,957 | 9/1962 | Chan ...................................... 2/444 |
| 3,182,658 | 5/1965 | Klinger .................................. 2/444 |
| 3,233,249 | 2/1966 | Baratelli et al. . |
| 3,233,250 | 2/1966 | Jonassen . |
| 3,368,221 | 2/1968 | Anderson ............................. 2/437 |
| 3,389,406 | 6/1968 | Mitchell . |
| 3,517,393 | 6/1970 | Beauchef . |
| 3,801,189 | 4/1974 | Bollé . |
| 3,945,044 | 3/1976 | McGee et al. . |
| 4,069,516 | 1/1978 | Watkins, Jr. . |
| 4,163,607 | 8/1979 | Nannini . |
| 4,353,134 | 10/1982 | Macnabb . |
| 4,425,669 | 1/1984 | Grendol et al. . |
| 4,504,127 | 3/1985 | Cottet . |
| 4,542,965 | 9/1985 | Shedrow ............................. 351/47 |
| 4,571,748 | 2/1986 | Carroll et al. . |
| 4,621,378 | 11/1986 | Hatchman . |
| 4,649,577 | 3/1987 | Wiedner ............................... 2/436 |
| 4,689,837 | 9/1987 | Bollé . |
| 4,707,863 | 11/1987 | McNeal ................................ 2/439 |
| 4,711,539 | 12/1987 | Krusas et al. ....................... 2/444 |
| 4,810,080 | 3/1989 | Grendol et al. . |
| 4,930,163 | 6/1990 | King ..................................... 2/444 |
| 4,934,807 | 6/1990 | Bollé . |
| 4,951,322 | 8/1990 | Lin . |
| 5,027,443 | 7/1991 | Watkins ............................... 2/447 |

FOREIGN PATENT DOCUMENTS

| | | |
|---|---|---|
| 2087403 | 12/1971 | France . |
| 9206658 | 4/1992 | WIPO .................................. 2/426 |

*Primary Examiner*—Clifford D. Crowder
*Assistant Examiner*—Michael A. Neas
*Attorney, Agent, or Firm*—Gregg I. Anderson; Holland & Hart

[57] ABSTRACT

A protective eyeshield (10) with detachable components is disclosed. The eyeshield consists of a detachable lens (11) maintained in a frame (12) by notches (46 and 48) on the lens which cooperate with brackets (50 and 51) on the frame and by insertion of the side edges (44) of the lens into slots (20) in the frame, The eyeshield is held in place on the head of the wearer by a strap (13) attached to a rotatable connector (14) attached to the frame, The connector's rotatability allows the position of the strap to be adjusted to the wearer. An optional eyeglass frame (15) having eyeglass lenses (68) mounted therein may be attached to the eyeshield frame to form a part of the eyeshield for simultaneous wearing of eyeglasses with the eyeshield.

14 Claims, 2 Drawing Sheets

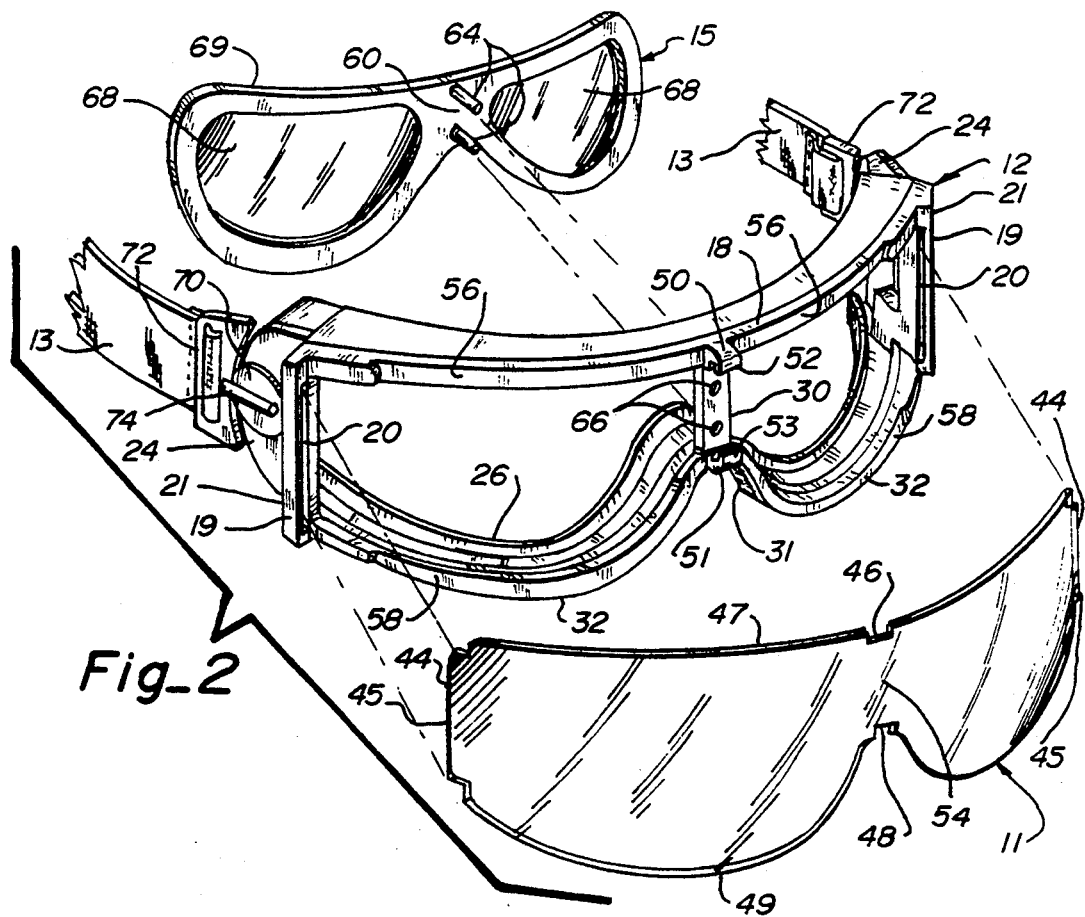
Fig_2
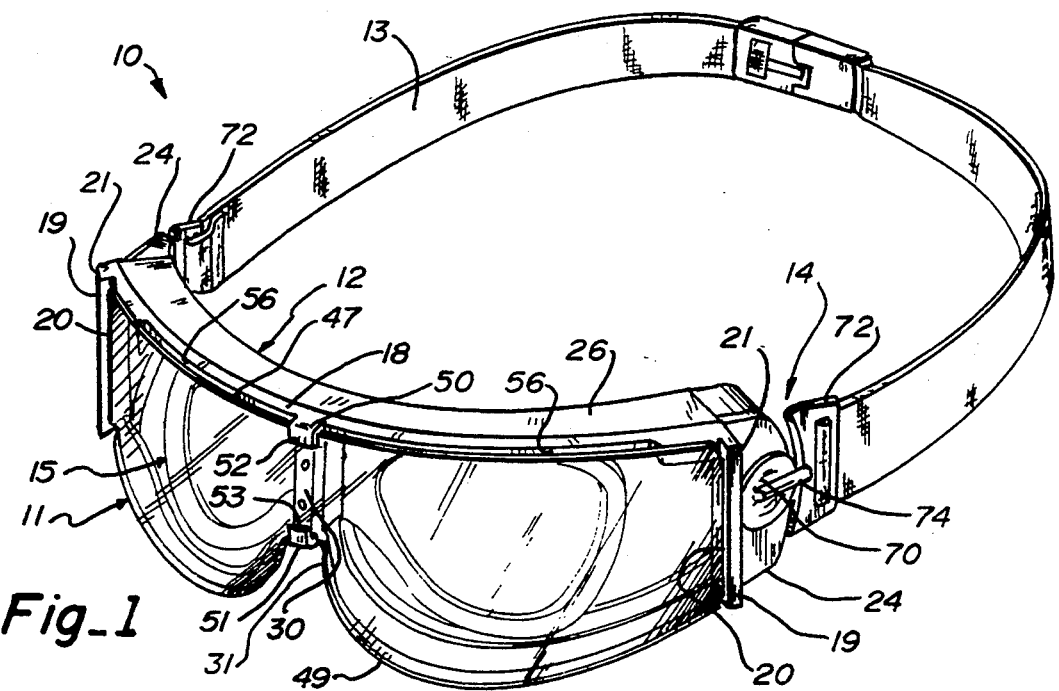
Fig_1

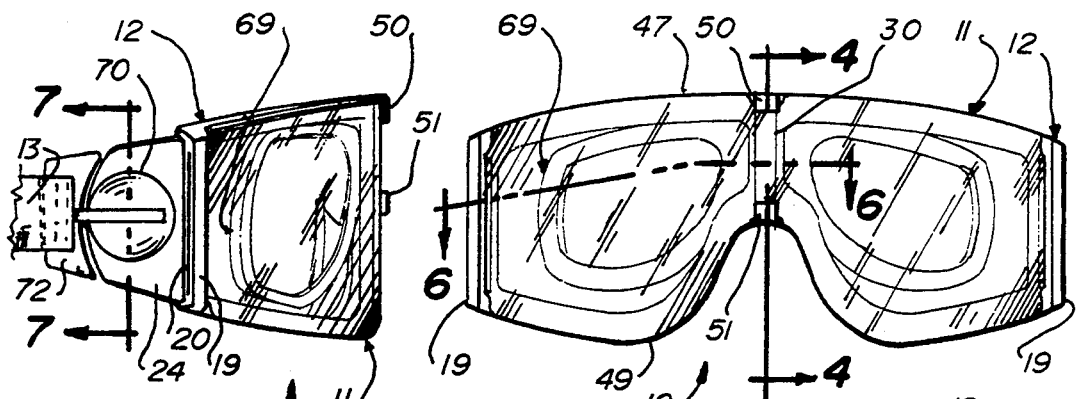
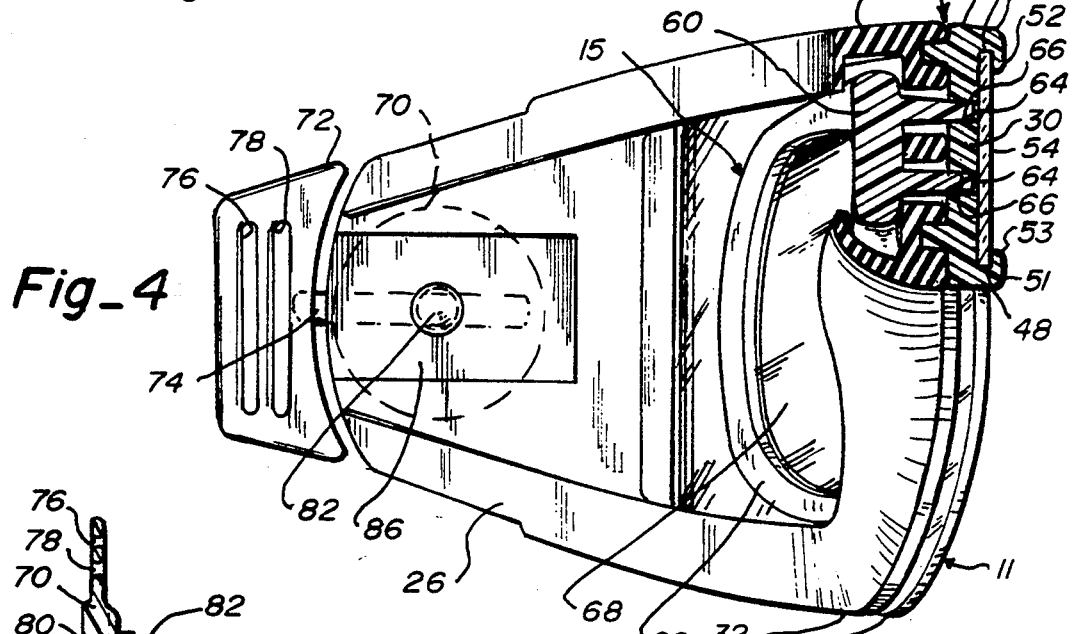
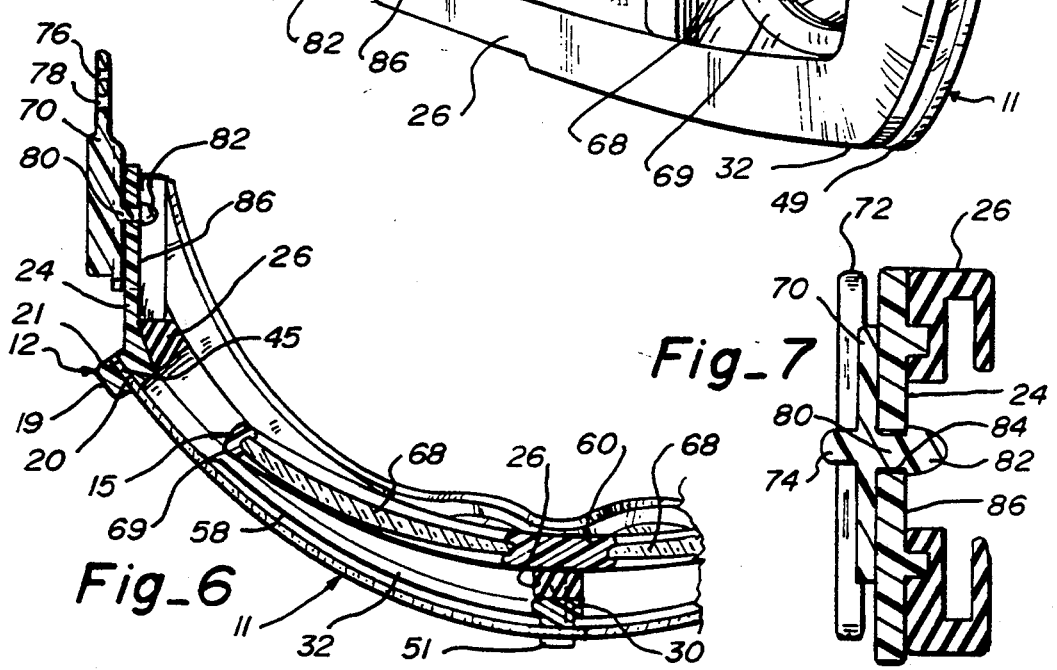

EYESHIELD WITH DETACHABLE COMPONENTS

FIELD OF THE INVENTION

The present invention relates to eyewear and especially to eye protecting shields with detachable components. More particularly the present invention relates to an improved eyeshield with a detachable lens to which eyeglasses such as prescription lenses may be attached.

BACKGROUND OF THE INVENTION

Sunglasses, eyeshields, and other eyewear have long been used for skiing and for other activities where eye protection is desired. Some sunglasses, eyeshields and other eyewear are made with detachable lenses to allow damaged lenses to be replaced and to allow the wearer to choose from among different colored lenses depending upon outside conditions. With some designs, however, the removal and replacement of lenses is unsatisfactory, such as when the frames are unduly rigid or have become misshapen and no longer mate accurately with the lenses to be inserted.

Moreover, prescription lenses are typically not designed to fit eyeshields. Persons desiring to wear eyeshields who regularly wear prescription eyeglasses often must wear their prescription eyeglasses underneath the eyeshields. Although some eyeshields provide sufficient room for prescription eyeglasses, wearing prescription eyeglasses under eyeshields can be uncomfortable due to pressure placed by the eyeshields or eyeshield straps on the ear piece of the prescription eyeglasses.

Other eyeshields do not satisfactorily provide for ventilation between the lens and the frame due to the method of attachment of the lens to the frame. When ventilation is lacking, eyeshields can fog, impairing the wearer's vision and endangering the wearer and others.

Eyeshields are often secured to the wearer by a strap which wraps around the back of the head of the wearer and which is attached to the sides of the eyeshield frame. This configuration can be uncomfortable for some wearers when the attitude of the strap causes the strap to be aligned over a bulky part of the wearer's headwear or hairstyle, such as when the wearer's hair is braided or tied in a bun. In such cases, the eyeshield must be angled uncomfortably on the wearer's face to align the strap above or below such obstructions.

OBJECTS OF THE INVENTION

It is the principal object of the present invention to provide an improved eyeshield having detachable components to allow the eyeshield to be used by persons with different needs such as persons requiring prescription lenses.

It is another object of the present invention to provide an improved eyeshield to which prescription lenses may be attached in a manner comfortable for the wearer.

It is a further object of the present invention to provide an improved eyeshield of the foregoing character which is comfortable to the wearer and affords adequate ventilation to preclude fogging of both the eyeshield and supported prescription lenses.

It is a still further object of the present invention to provide an improved eyeshield having the aforementioned qualities which is rugged and which is economical to produce.

SUMMARY OF THE INVENTION

In accordance with the present invention, an eyeshield is disclosed in which a strap for holding the eyeshield on the head of the wearer is attached to the frame of the eyeshield by a connector which may be rotated to adjust the position of the strap on the wearer's head. The lens of the eyeshield of the present invention may be easily detached, and is held in place by cooperating notches on the lens and slots and brackets on the frame of the eyeshield. Space for ventilation is maintained between the lens and the frame. A separate set of eyeglasses may be attached to the interior frame so as to form a part of the eyeshield for simultaneous wearing of the eyeglasses and the eyeshield without undue discomfort to the user.

Other aspects, features and details of the present invention can be more completely understood by reference to the following detailed description of the preferred embodiment, taken in conjunction with the drawings, and from the appended claims.

BRIEF DESCRIPTION OF THE DRAWINGS

FIG. 1 is an isometric view of the eyeshield of the present invention with an eyeglass frame attached thereto.

FIG. 2 is an exploded view of the eyeshield and eyeglass frame shown in FIG. 1.

FIG. 3 is a frontal view of the eyeshield and eyeglass frame shown in FIGS. 1 and 2.

FIG. 4 is a section taken in the plane 4—4 of FIG. 3.

FIG. 5 is a right side view of the eyeshield shown in FIGS. 1, 2 and 3.

FIG. 6 is a section taken in the plane 6—6 of FIG. 3.

FIG. 7 is a section taken in the plane 7—7 of FIG. 5.

DETAILED DESCRIPTION

A preferred embodiment of the eyeshield 10 of the present invention is shown in FIGS. 1 and 2. The eyeshield 10 includes a eyeshield lens 11 which is supported on a frame 12 and which is detachable from the frame. Space between the frame and the lens provides ventilation during use and prevents fogging of the lens. The lens 11 and frame 12 are held in place on the head of the wearer by an elastic strap 13 wrapped around the back of the head of the wearer which is attached to opposite ends of the eyeshield by a rotatable connector 14. The rotatable connector 14 allows the strap 13 to be adjustably positioned on the head of the wearer in a manner most comfortable to the wearer. A detachable eyeglass frame 15 without ear pieces may be worn with and attached to the eyeshields 10 when corrective lenses or additional glare protection is required by the wearer.

The frame 12 of the eyeshield 10 is formed of a scratch resistant plastic and molded into a forwardly convex shape. The frame has a substantially horizontal upper edge 18, two relatively straight vertical sides 19, and a lower edge 32. (As used herein, "horizontal", "vertical" and similar terms describing aspects of the present invention are interpreted as if the eyeshields are aligned as if positioned on a wearer during use.) A vertical forwardly opening slot 20 is formed in outwardly protruding portions 21 of each of the sides of the frame for releasably retaining the lens 11, as further described below. Rearward arcuate extensions 24 are formed on a rear face of sides 19 to which the strap 13 is rotatably attached by the connector 14, as is also further described below.

Mounted on the inside of the frame 12 around the perimeter of the frame is a relatively soft cushion 26 which forms a seal with the face of the wearer. Although the cushion 26 is preferably mounted to the frame 12 with an adhesive, other means of attachment may be employed, and are well known in the art. For example, a channel may be formed in the frame 12 into which, at elevated temperatures, fluidized cushion material is allowed to flow for permanent retention therein. In any case, the cushion 26 is typically formed to define an inwardly facing u-shaped channel, in cross-section as best seen in FIG. 7, which allows the cushion to conform to the structure of the wearer's face.

In the center of the upper edge 18 of the frame 12, the frame extends downwardly to form a bridge 30 approximately 1¼" in length which connects with an upwardly arcuate portion 31 of the lower edge 32 of the frame 12, the arcuate portion 31 being shaped to conform with the wearer's nose. The bridge 30 provides structural support for the frame 12, supports the lens 11 of the eyeshield 10, and also supports the optional eyeglasses frame 15 which may be worn with the eyeshield 10.

The lens 11 is typically manufactured from a clear or tinted plastic which is not readily susceptible to breakage or scratching, such as polycarbonate. In the preferred embodiment the lens 11 is of a slightly convex construction which maximizes the wearer's peripheral vision when wearing the eyeshield 10, as shown in FIGS. 1, 2 and 6. Alternatively, the lens 11 may be substantially flat, in which case the frame extensions 24 may be placed substantially perpendicular to the plane of the lens 11, or the lens may be of another shape well known in the art. Whatever the lens shape, side edges 44 of the lens 11 (FIG. 1) extend to form tabs 45 of reduced height relative to the remainder of the lens, which are insertable into the slots 20 in the sides 19 of the frame 12. Although in the preferred embodiment, due to the reduced height of the tabs 45, notches are defined in the corners of the side edges 44, the corners need not be notched so long as the length of each side edge 44 is less than or substantially equal to the length of the corresponding slot 20 of the frame 12 into which it is to be inserted. The side edges 44 or tabs 45 (as the case may be) may be inserted into and removed from the slots 20 by pressing the side edges 44 towards each other, thereby causing the lens 11 to bow.

An upper notch 46 approximately ¼" wide and ⅛" deep is formed in an upper edge 47 of the lens 11 at the longitudinal center of the lens and a lower notch 48 approximately ¼" wide and ⅛" deep is formed in the lower edge 49 of the lens at the longitudinal center of the lens. The upper notch 46 is inserted under an inverted L-shaped upper bracket 50 extending forwardly from an upper portion of the bridge 30 and the lower notch 48 is inserted under an L-shaped lower bracket 51 extending from a lower portion of the bridge 30 (FIGS. 2 and 4). The brackets 50 and 51 cooperate with the notches 46 and 48 to firmly hold the lens 11 in place on the frame 12. Each bracket 50 and 51 extends outwardly (away from the lens) approximately 1/16" and opens towards the other bracket. Legs 52 and 53 of the upper and lower brackets 50 and 51 respectively are approximately ⅛" long and are spread apart to allow insertion of a center portion 54 of the lens 11 therebetween. If sufficiently flexible, the legs 52 and 53 of the upper and lower brackets 50 and 51 may be pushed apart to accommodate the lens 11. Alternatively, if the frame 12 is sufficiently flexible, the upper and lower edges 18 and 32 of the frame 12 may be pinched towards each other so as to bow the bridge 30 outwardly and cause the upper and lower brackets 50 and 51 to separate sufficiently to allow insertion of the lens 11 therebetween.

To allow for ventilation between the lens 11 and the frame 12, elongated rectangular notches 56 and 58 are formed in the front face of the upper edge 18 and the lower edge 32 of the frame 12 (FIG. 1). Each notch 56 begins near the bridge 30 and extends laterally along the upper edge 18 ending approximately ⅜" before the upper edge intersects one of the sides 19. Each notch 58 begins near the bridge 30 and extends laterally along the lower edge 32 ending approximately ⅜" before the lower edge intersects one of the sides 19. The notches are approximately ⅛" deep throughout. Although contact is maintained between the side edges 44 or tabs 45 of the lens 11 and the slots 20 of the frame 12 and between the bridge 30 and the center portion 54 of the lens, space is created between the notches 56 and 58 and the lens 11. In this way, the lens 11 is spaced from the frame 12, providing air passages for ventilation to prevent the lens from fogging during use which could result in impairment of the wearer's vision and risk injury to the wearer or others.

The eyeglass frame 15 worn with the eyeshield (FIGS. 1-4) does not have ear pieces which are conventionally used to hold eyeglass frames in position during use. Instead, to avoid discomfort to the wearer which might otherwise result from the ear pieces rubbing against the eyeshield 10 or the eyeshield strap 13, a bridge 60 of the eyeglass frame 15 is detachably mounted to the rear face of the eyeshield bridge 30.

In a preferred embodiment as detailed in FIG. 4, a pair of vertically aligned forwardly projecting pins 64 are formed into the bridge 60 of the eyeglass frame and are adapted to be frictionally received in a pair of vertically aligned holes 66 formed in the rear face of the bridge 30 of the eyeshield frame. In the preferred embodiment, the pins 64 each have a diameter which decreases towards the tip of each pin so that the eyeglass frame 15 is positioned on the eyeshield 10 by pressing the eyeglass frame against the eyeshield bridge 30 to frictionally engage the pins 64 in the holes 66. To remove the eyeglass frame 15 from the eyeshield 10, the eyeglass frame is grasped and pulled away from the eyeshield.

In one alternative embodiment (not shown) the diameter of each pin 64 is constant. In another alternative embodiment (not shown) the pins 64 each have an enlarged tip, the holes 66 each having a complementary pocket for retention of the pins 64. In this embodiment, the enlarged tip of each pin 64 is formed of a sufficiently compressible material to allow the enlarged tip to be inserted into the holes 66 and retained until such time as the wearer separates the eyeglass frame 15 from the eyeshields 10 by pulling them apart. In each of these embodiments, holes must also be formed through the flexible cushion 26 which lines the inside of the frame 12 in alignment with the holes 66 to allow insertion of the pins 64 into the holes 66. Alternatively, other forms of attachment of the eyeglass frame 15 to the eyeshields 10 may be employed, such as cooperating magnetic or VELCRO fasteners strips, for example.

The eyeglass frame 15 may contain prescription lenses 68 especially suited for the wearer or may contain clear or tinted non-prescription lenses. The lenses 68 are retained in the eyeglass frame 15 by a rim 69 of the eyeglass frame. As can be appreciated from the preceding description, a person wearing the eyeshield 10 of the present invention may combine a particular eyeshield lens 11 with or without an eyeglass frame 15, in a custom configuration based upon the activity contemplated by the wearer, the external conditions, and the wearer's need for corrective eyeware.

In the preferred embodiment shown in FIGS. 5, 6 and 7, the strap 13 is attached to the extensions 24 of the sides 19 of the frame 12 by the rotatable connector 14. The connector 14 includes a hub 70 and a tab 72 which is integrally connected to the hub by an arm 74. The connector 14 also contains slots 76 and 78 through which the strap 13 is inserted and affixed to the connector. The hub 70 is rotatably attached to the extension 24, thus allowing the strap 13 to comfortably wrap around the wearer's head at angles at, above or below the level of the upper edge 18 of the frame 12 of the eyeshields 10. In the preferred embodiment, the hub 70 of the connector 14, which maintains the connector in a position substantially parallel to the extension 24, has a pin 80 extending inwardly and perpendicularly from the underside of the hub. The pin 80 has an enlarged boss on its free end 82. The boss 82 of the pin 80 is inserted into a circular hole 84 formed in the extension 24. The hole 84 has a diameter slightly larger than that of the pin 80 and slightly less than that of the boss 82 of the pin to prevent the boss from undesired detachment from the hole 84. The boss 82 is preferably formed of a flexible plastic having a slight compressibility so that the boss can be inserted through or removed from the hole 84 with application of slight pressure or of a slight pulling motion.

To avoid discomfort to the wearer resulting from contact between the connector 14 and the wearer, the cushion 26 which creates a seal between the eyeshield 10 and the face of the wearer is formed sufficiently thick over the extensions 24 to prevent contact between the connector and the wearer. In addition, contact between the cushion 26 and the connector 14 is prevented by formation of a recess 86 in the cushion 26, thus allowing freedom of rotational movement of the connector 14 during use.

While certain illustrative embodiments of the present invention have been shown in the drawings and described above in considerable detail, it should be understood that there is no intention to limit the invention to the specific form disclosed. On the contrary, the invention is to cover all modification alternatives, equipment, and uses falling within the spirit and scope of the invention as expressed in the appended claims.

What is claimed is:

1. Protective eyewear comprising:
   a lens having a peripheral edge formed thereabout, the peripheral edge of said lens defined by opposing, upstanding side edge portions of said lens, a horizontally-extending top edge portion of said lens, and a horizontally-extending bottom edge portion of said lens, the top edge portion having an upper notch formed substantially midway along the length thereof, and the bottom edge portion having a lower notch formed substantially midway along the length thereof in vertical alignment with the upper notch;
   a flexible frame for maintaining the lens in a spaced apart relation to the wearer's face, the frame further comprising:
   an upper bracket attached thereto for releasably retaining the top edge portion of the lens near the upper notch formed therealong;
   a lower bracket attached thereto for releasably retaining the bottom edge portion of the lens near the lower notch formed therealong; and
   opposing slots formed in the frame for releasably retaining the opposing, upstanding side edge portions of the lens wherein the lens, when retained by said flexible frame, contacts with the flexible frame along the opposing, upstanding edge portions and at the upper and lower notches, respectively, of the peripheral edge thereof and is spaced-apart from the frame along remaining portions of the peripheral edge thereof; and
   a mounting member for maintaining the frame with attached lens on the head of the wearer.

2. Protective eyewear as in claim 1 wherein the upper and lower brackets are L-shaped each having a leg extending towards the leg of the other bracket.

3. Protective eyewear as in claim 2 wherein the frame further includes:
   a peripheral frame edge; and
   a bridge centrally located on the frame and extending between opposing portions of the peripheral frame edge; and wherein the upper and lower brackets are mounted on the bridge in a spaced configuration.

4. Protective eyewear as in claim 3 wherein the frame edge further includes notch means formed in the frame edge creating a gap between the frame and the lens to provide ventilation between the lens and the wearer's face.

5. Protective eyewear as in claim 1 wherein the frame further comprises:
   notch means formed in the frame creating a gap between the frame and the lens to provide ventilation between the lens and the wearer's face.

6. Protective eyewear as in claim 5 wherein the notch means further includes:
   a plurality of spaced notches formed in opposing locations in the frame.

7. Protective eyewear as in claim 6 wherein the frame includes opposing sides and the mounting member comprises:
   an elongated strap to wrap around the head of the wearer, the strap having opposing ends attached to the opposing sides of the frame.

8. Protective eyewear comprising:
   a lens having a horizontally-extending top-side edge and a horizontally-extending bottom side edge;
   a flexible frame for maintaining the lens in a spaced apart relation to the wearer's face, the frame having a peripheral edge including an upper edge, a pair of side edges, and a lower edge, and an attachment device centrally located on each of the upper and lower edges for attaching the lens to the frame, the frame having a notch member formed therein for creating a gap between the frame and the lens to provide ventilation between the lens and the wearer's face, said notch member including an upper notch portion extending substantially the entire length along the upper edge between the attachment device and each of the side edges and a lower notch portion extending substantially the entire length along the lower edge between the attachment device and each of the side edges whereat the top-side edge and the bottom-side edge of the lens contacts with only the attachment device of the flexible frame and is maintained in a spaced-apart relationship with the flexible frame along remaining portions of the top-side edge and the bottom-side edge, thereby creating a gap between the flexible frame and the lens to provide ventilation between the lens and the wearer's face; and a mounting member for maintaining the frame with attached lens on the head of the wearer.

9. A protective eyeshield comprising:

a lens having a peripheral edge formed thereabout, the peripheral edge of said lens defined by opposing upstanding side edge portions of said lens, a horizontally-extending top edge portion of said lens, and a horizontally-extending bottom edge portion of said lens, the top edge portion having an upper notch formed substantially midway along the length thereof, and the bottom edge portion having a lower notch formed substantially midway along the length thereof in vertical alignment with the upper notch;

an eyeshield frame for maintaining the lens in a spaced relation to the wearer's face, said eyeshield frame having upper and lower brackets for retaining the top and bottom edge portions, respectively, of the lens near the upper and lower notches, respectively, thereof, and opposing side slots for retaining the upstanding side edge portions of the lens, such that the lens contacts with the frame near the upper and lower notches and along the opposing, upstanding side edge portions of the lens and is spaced-apart from the frame along remaining portions of the peripheral edge thereof, and defining a hole therein;

a maintaining device for maintaining the eyewear on the head of the wearer; and an eyeglass frame including a rim, eyeglass lenses secured in the rim, and a pin extending forwardly from the eyeglass frame and adapted for releasable engagement with the hole defined in the eyeshield frame so as to releasably attach the eyeglass frame to the eyeshield frame.

10. The protective eyeshield of claim 9 wherein the pin is tapered.

11. The protective eyeshield of claim 9 wherein the pin further includes an enlarged tip and wherein the cooperating hole includes a complementary pocket for releasably retaining the enlarged tip.

12. The protective eyeshield of claim 9 wherein said eyeshield frame defines a second hole therein and wherein said eyeglass frame includes a second pin protruding forwardly from the eyeglass frame and adapted for releasable engagement with said second hole defined in the eyeshield frame.

13. A protective eyeshield, comprising:

a lens having a peripheral edge including opposing upstanding side edge portions, a horizontally-extending top edge portion having an upper lens notch and a horizontally-extending bottom edge portion having a lower lens notch;

a flexible frame for maintaining the lens in a spaced apart relation to the wearer's face, the frame defining a frame notch formed therein for creating a gap between the frame and the lens to provide ventilation between the lens and the wearer's face, the frame further comprising:

an upper bracket attached thereto for releasably retaining the top edge portion of the peripheral edge of the lens near the upper lens notch;

a lower bracket attached thereto for releasably retaining the bottom edge portion of the peripheral edge of the lens near the lower lens notch; and opposing slots formed in the frame for releasably retaining the opposing upstanding side edge portions of the lens such that the lens contacts with the frame along the opposing upstanding edge portions and at the upper and lower lens notches, respectively, of the lens and is spaced-apart from the frame by the gap created between the frame and the lens by the frame notch;

an eyeglass frame including a rim, eyeglass lenses secured in the rim and a connector for releasably attaching the eyeglass frame to the eyeshield frame;

an elongated strap having opposed ends; and a pair of connector elements for rotatably attaching the opposing ends of the strap to spaced locations on the frame to adjustably maintain the eyewear on the head of the wearer.

14. A protective eyeshield comprising:

a lens;

an eyeshield frame for maintaining the lens in a spaced relation to the wearer's face and defining a first hole and a second hole therein, said first hole and said second hole being centrally-located and vertically-aligned on said eyeshield frame;

means for maintaining the eyewear on the head of the wearer; and an eyeglass frame including a rim and eyeglass lenses secured in the rim, and a first pin and a second pin, centrally-located and vertically-aligned to extend forwardly from said eyeglass frame for releasably engaging with the first hole and said second hole, respectively, defined in said eyeshield frame so as to releasably attach the eyeglass frame to the eyeshield frame.

* * * * *